(12) United States Patent
Gloriant et al.

(10) Patent No.: US 9,677,162 B2
(45) Date of Patent: Jun. 13, 2017

(54) METHOD FOR MANUFACTURING A TITANIUM ALLOY FOR BIOMEDICAL DEVICES

(71) Applicants: INSTITUT NATIONAL DES SCIENCES APPLIQUEES DE RENNES, Rennes (FR); CENTRE NATIONAL DE LA RECHERCHE SCIENTIFIQUE, Paris (FR)

(72) Inventors: Thierry Gloriant, Mouaze (FR); Doina Gordin, Mouaze (FR)

(73) Assignees: INSTITUT NATIONAL DES SCIENCES APPLIQUEES DE RENNES, Rennes (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 381 days.

(21) Appl. No.: 14/357,559

(22) PCT Filed: Nov. 7, 2012

(86) PCT No.: PCT/FR2012/052572
§ 371 (c)(1),
(2) Date: May 9, 2014

(87) PCT Pub. No.: WO2013/068691
PCT Pub. Date: May 16, 2013

(65) Prior Publication Data
US 2014/0338795 A1 Nov. 20, 2014

(30) Foreign Application Priority Data

Nov. 10, 2011 (FR) ...................................... 11 60281

(51) Int. Cl.
*C22F 1/18* (2006.01)
*C23C 8/24* (2006.01)
(Continued)

(52) U.S. Cl.
CPC .............. *C22F 1/183* (2013.01); *A61L 27/06* (2013.01); *A61L 29/02* (2013.01); *A61L 31/022* (2013.01);
(Continued)

(58) Field of Classification Search
CPC . C22F 1/183; C22F 1/006; C23C 8/30; C23C 8/24
See application file for complete search history.

(56) References Cited

FOREIGN PATENT DOCUMENTS

| EP | 0449793 A1 | 10/1991 |
|---|---|---|
| EP | 0601804 A1 | 6/1994 |

(Continued)

OTHER PUBLICATIONS

Biesiekierski, Arne, et al. "A new look at biomedical Ti-based shape memory alloys." Acta biomaterialia 8.5 (2012): 1661-1669.*

(Continued)

*Primary Examiner* — Jessee Roe
(74) *Attorney, Agent, or Firm* — Gordon Rees Scully Mansukhani LLP; David R. Heckadon

(57) ABSTRACT

The invention relates to a method for manufacturing a titanium alloy having superelastic properties and/or shape memory for biomedical use, which comprises the steps of: preparing an ingot by melting the various metals that form the desired alloy in a vacuum; optionally homogenizing the ingot in a vacuum by high-temperature annealing (higher than 900° C.); first quenching; mechanical shaping (rolling, drawing, machining or the like); heat treatment for redissolution in beta phase beyond the beta transus temperature (until a second temperature and then maintaining same for a certain time); and second quenching; characterized in that said heat treatment phase is carried out in a gaseous atmo- (Continued)

sphere and also constitutes a surface treatment suitable for forming on the surface a layer of nitride, carbonitride, oxide, oxynitride or the like.

9 Claims, 2 Drawing Sheets

(51) Int. Cl.
C22C 1/02 (2006.01)
C22C 14/00 (2006.01)
A61L 27/06 (2006.01)
A61L 29/02 (2006.01)
A61L 31/02 (2006.01)
C23C 8/28 (2006.01)
C23C 8/30 (2006.01)

(52) U.S. Cl.
CPC .............. *C22C 1/02* (2013.01); *C22C 14/00* (2013.01); *C23C 8/24* (2013.01); *C23C 8/28* (2013.01); *C23C 8/30* (2013.01); *A61C 2201/007* (2013.01); *A61L 2400/16* (2013.01); *C21D 2201/01* (2013.01); *C21D 2201/02* (2013.01); *F04C 2270/0421* (2013.01)

(56) References Cited

FOREIGN PATENT DOCUMENTS

FR 2848810 A1 6/2004
WO WO2013068691 A1 5/2013

OTHER PUBLICATIONS

International Search Report for International Application No. PCT/FR2012/052572; Jan. 16, 2013, pp. 1-4, EPO, Rijswijk, NL.
Written Opinion of the International Search Authority for International Application No. PCT/FR2012/052572; May 10, 2014; pp. 1-6, EPO, Rijswijk, NL.
International Preliminary Report on Patentability Chapter I for International Application No. PCT/FR2012/052572; May 13, 2014. pp. 1-7, Geneva, Switzerland.

\* cited by examiner

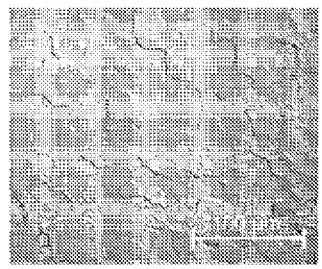
Fig. 2
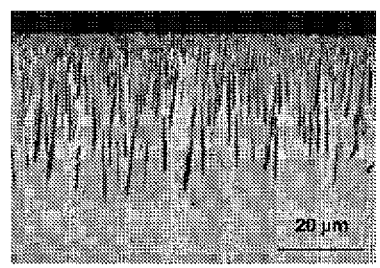
Fig. 3
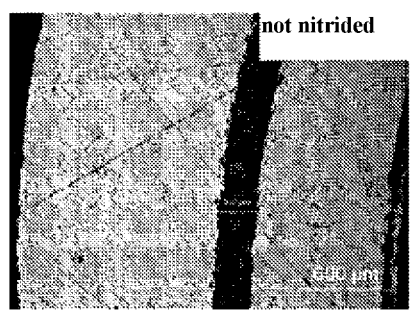 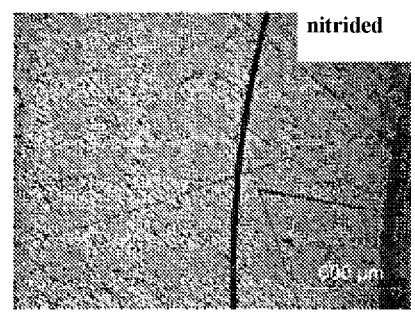
Fig. 5A     Fig. 5B

METHOD FOR MANUFACTURING A TITANIUM ALLOY FOR BIOMEDICAL DEVICES

CROSS-REFERENCE TO RELATED APPLICATIONS

This application is a United States national stage entry of International Application serial no. PCT/FR2012/052572 filed Nov. 7, 2012, which claims priority to French Patent Application Serial No. FR1160281 filed Nov. 10, 2011. The contents of both of these prior applications are incorporated herein by reference in their entirety as if set forth verbatim.

FIELD

The invention relates to a method for manufacturing a titanium alloy having superelastic and/or shape memory properties, intended for making devices used in the biomedical area, such as for example endodontic files, arcs, wires and orthodontic springs, dental implants, cardiovascular or pulmonary stents, guide wires and catheters for cardiovascular surgery, staples and joint prostheses for orthopedic surgery.

The invention also relates to an alloy obtained using the method, as well as biomedical devices incorporating such an alloy.

BACKGROUND

In the biomedical field, devices and elements such as those listed above as examples need to have very different characteristics, firstly from the mechanical standpoint in view of the objective of acting on a part of the human body (such as a tooth, for example, as part of an orthodontic application) and secondly from the biological standpoint, to avoid or minimize the reactions or consequences relating to contact by the device with the part of the human body or organ.

Some of the technical characteristics that are sought or even necessary include the largest possible recoverable elasticity range (property of superelasticity), low rigidity, excellent chemical biocompatibility, high resistance to corrosion and sterilization products, ease of machining and cold work, and increased hardness and resistance to surface wear.

In a known manner, attempts have been made to reconcile these constraints, which are generally contradictory with each other. The superelastic and/or shape memory alloys that are currently in use in the biomedical area are of the titanium-nickel type.

However, it is known that nickel is allergenic for the body and can lead to inflammatory reactions, in spite of the usefulness of its mechanical properties, particularly those of superelasticity and/or shape memory. Besides, Ti—Ni alloys offer mediocre machinability, leading to the premature breaking of endodontic files (see for example: Oiknine M., Benizri J., REV. ODONT. STOMATO. 36 (2007) 109-123) and are sometimes difficult to form when cold.

These known alloys have a superelastic property because of stress-induced destabilization of the (cubic) parent beta phase by transformation into a reversible (orthorhombic) alpha" martensitic phase (Kim H. Y., Ikehara Y., et al, ACTA MATERIALIA 54 (2006) 2419-2429).

Further, nickel-free titanium alloys (called 'Gum Metals', Saito T., Furuta T. et al, SCIENCE 300 (2003) 464-467) are known and are considered to be superelastic, because even if they do not show martensitic transformation under stress, they have low rigidity and very high recoverable elasticity.

Besides, nickel-free titanium alloys are known in the French patent 2 848 810, the U.S. patent application 2007/0137742 and the patent application WO 2005/093109.

Nevertheless, the alloys proposed in that prior art do not satisfactorily meet all the required criteria overall, both in terms of their mechanical properties and those of biocompatibility, particularly at the surface.

For example, in respect of biological compatibility, the French patent above offers a surface treatment of the alloy by depositing nitride, using a plasma based technique.

However, this known technique is not satisfactory. Plasma depositing does not make it possible to deposit an even coat of nitride. That has harmful or adverse consequences in the case of devices or elements with particular shapes or parts or areas that are not easily accessible (such as concavities or the like).

Further, the French patent describes a method that does not apply to a shape memory and/or superelastic alloy.

While most alloys are therefore made from titanium and nickel, superelastic alloys made from nickel-free titanium have been proposed recently, which are particularly easily deformable when cold. The article in the JOURNAL OF THE MECHANICAL BEHAVIOR OF BIOMEDICAL MATERIALS 3 (2010) 559-564, by Bertrand E., Gloriant T. et al "Synthesis and characterisation of a new superelastic Ti-25Ta-25Nb biomedical alloy" shows such nickel-free titanium alloys.

Thus, the method according to the invention makes it possible to solve the problems of the prior art by proposing the manufacture of a titanium alloy for biomedical applications with superelastic and/or shape memory properties and surface treatment, which meets all the mechanical conditions stated above and which is further an improvement on the prior art as regards surface hardness, ease of cold working and machining, and also resistance to sterilization, while being also perfectly biocompatible.

SUMMARY

To that end, according to the invention, the method for manufacturing a titanium alloy with no nickel and with superelastic and/or shape memory properties for biomedical applications, is of the type comprising the successive phases of:

preparing an ingot by vacuum melting the different metals that make up the required alloy;

vacuum homogenizing of the ingot by annealing at a first temperature, particularly above 900° C., consisting in raising the temperature of the ingot and holding it at that temperature for a period that allows full homogenization first quenching;

mechanical shaping at ambient temperature, such as by rolling, drawing, machining or the like;

heat treatment for redissolution in beta phase beyond the beta transus temperature consisting in raising the temperature up to a second required temperature and holding at that temperature for a certain period second quenching;

characterized in that said heat treatment phase is carried out in a gaseous atmosphere and also constitutes a phase known as nitriding where surface treatment is applied through a reaction with said gas, so as to form a coat of nitride, carbonitride or oxynitride evenly on the surface.

The ingot obtained during the first step has a mass varying from a few tens to a few hundred grams for making the biomedical device.

Advantageously, said gas is nitrogen.

Thus, the method according to the invention introduces a surface treatment step (by nitriding in gaseous phase) in order to improve the mechanical and surface biocompatibility proprieties of the alloy.

During the nitriding step, care is taken to install the shaped ingot in an enclosure so that its arrangement allows the depositing of the coat in gaseous phase on the totality of the surface, including in the concavities of the shaped ingot. To that end, the ingot is suspended by a chain in the center of the enclosure making up the stove.

The first and second quenches are aimed at retaining the beta phase at ambient temperature, in order to achieve the required superelastic effect. Depending on the composition of the alloy, quenching is carried out either with water or with air.

The homogenizing phase is optional in that for certain alloy compositions, the fusion phase may lead directly to the obtaining of an even ingot. The homogenizing phase is carried out at a temperature above 900° C.

Besides, it is known that the beta transus temperature is the lowest temperature at which a 100% beta phase of the alloy can exist. It varies between 600° C. and 1050° C., depending on the composition of the alloy.

Preferably, the simultaneous phase of redissolution in beta phase and nitriding (if the gas is nitrogen) is carried out at a temperature ranging between 600 and 1050° C., preferably between 800° C. and 1050° C., in a gaseous atmosphere, preferably nitrogen, for a duration of several hours, in order to obtain a surface coat of nitride varying from a few microns to a few tens of microns thick, depending on the intended use.

The duration of holding at the annealing temperature of the homogenizing phase ranges between 12 and 20 hours, preferably about 16 hours.

As an alternative, the nitride coat (or any other type of coat) may be made using a technique of the type:
- plasma
- ion implantation
- cathode arc
- laser
- any PVD or CVD method.

The technique used must not modify the beta metastable microstructure of the alloy that is at the origin of the superelastic effect.

Advantageously, the nitriding phase is combined with a simultaneous phase of recrystallization and leads to the making of a recrystallized beta microstructure.

The invention also relates firstly to an alloy such as that obtained by the method above, and secondly a device for biomedical use incorporating said alloy.

In a preferred form, the alloy according to the invention comprises the following by atomic percentage depending on its chemical composition
- Titanium: 30% to 98%
- Niobium: 0% to 40%
- Molybdenum: 0% to 15%
- Chrome: 0% to 15%
- Iron: 0% to 15%
- Zirconium: 0% to 40%
- Hafnium: 0% to 40%
- Tantalum: 0% to 60%
- Oxygen: 0% to 2%
- Nitrogen: 0% to 2%
- Silicon: 0% to 2%
- Boron: 0% to 2%
- Carbon: 0% to 2%
- Vanadium: 0% to 15%
- Tungsten: 0% to 20%
- Aluminum: 0% to 10%
- Tin: 0% to 10%
- Gallium: 0% to 10%

Below are a few compositions of the alloy according to the invention, given by atomic percentage:
Ti74 Nb26
Ti72 Nb18 Ta10
15 Ti74 Nb20 Zr6
Ti76 Nb23 N
Ti78.5 Nb15 Zr2.5 Sn4
Ti73.1 Nb23 Ta0.7 Zr2 O1.2

Thus, unlike the prior art, the alloy according to the invention does not contain nickel.

The invention will be better understood from the description below of illustrative but non-limitative examples by reference to the accompanying drawings wherein:

BRIEF DESCRIPTION OF THE DRAWINGS

FIG. 2 is a micrograph obtained with an optical microscope showing the beta metastable microstructure of the core of an example of Ti-25Ta-25Nb alloy.

FIG. 3 shows a cross-section observed through an optical microscope of the nitrided surface microstructure of the alloy in FIG. 2.

FIGS. 5A and 5B show micrographs obtained by optical microscopy of a non-nitrided (prior art) sample and a nitrided (invention) sample respectively, after scratch testing by pin on disc tribometer with equivalent loads and numbers of cycles.

DETAILED DESCRIPTION

The invention is now described by reference to FIG. 1, which shows a schematic curve of the temperature variations of an ingot including the different compounds and intended to form the alloy as a function of time by reference to the successive steps of the method according to the invention.

In a preliminary step (not shown in FIG. 1), the different quantities of metals that are to go into the composition of the alloy to make are brought together in the proportions defined below. The mixture of metals is subjected to a preliminary fusion operation at a temperature between 2000° C. and 3000° C. Advantageously, this preliminary fusion step is carried out in a cold crucible using magnetic semi-levitation and a high-frequency induction generator. Conventional or flash sintering techniques may also be used.

During this preliminary stage, it is important to make sure a homogeneous mixture is made, with no inclusion or contamination or pollution with foreign elements. In that respect, melting is preferably carried out in a vacuum or a controlled atmosphere with inert gas (such as argon for example).

The different elements that are liable to enter into the composition of the ingot and thus the future alloy include:
  titanium, for a large or the most part
  other metals, such as tantalum, niobium, molybdenum, zirconium, hafnium, vanadium, iron, chrome, tungsten, which are known as beta-stabilizing elements and possibly
  yet other elements such as aluminum, silicon boron, carbon, oxygen, nitrogen, tin, gallium etc. which, when added in small quantities, are liable to improve the superelastic properties.

The different components are selected in qualitative and quantitative terms in order to make a beta metastable type alloy by quenching, and allowing the formation of an alpha" martensitic phase that is reversible, and thus giving superelastic and/or shape memory properties.

The beta metastable nature of the alloy is reflected in a low elasticity modulus, which varies from 10 GPa to 70 GPa and is close to that of bone. From the melted ingot obtained in the preliminary melting step mentioned above, the second step consists in "homogenizing annealing" at high temperature (typically between 900° C. and 1200° C.) under ultra-high vacuum.

Figure 1:
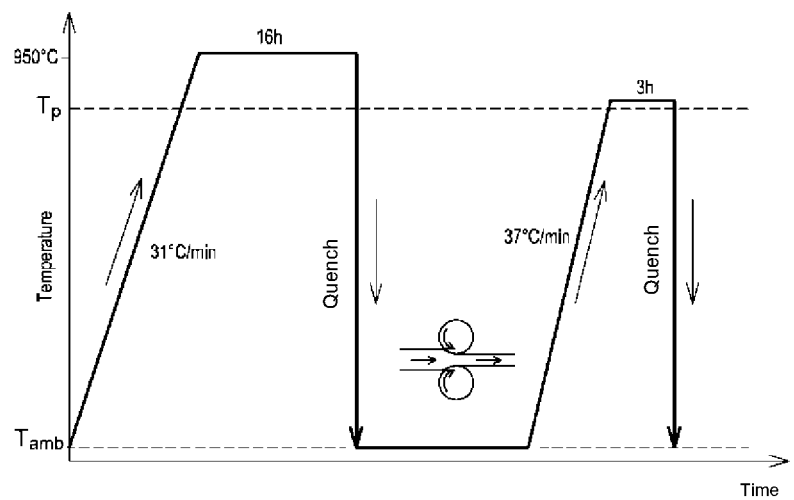
FIG. 1 is a graph representing variation as a function of time of the temperature to which the alloy ingot is subjected in the different steps of the method according to the invention.

Note that in the chart of FIG. 1, the time scale (abscissa) is not followed for practical reasons.

The ingot is kept at the said annealing temperature for a period that may be several hours long. The treatment temperature and duration depend on the alloy in question. Ultimately, a completely homogeneous alloy must be obtained.

The homogenizing annealing phase ends in a first quench, preferably in water, so as to retain a beta microstructure that is metastable at the ambient temperature, to favor shaping operations. Quenching is carried out in a fraction of a second by dropping the ingot at the annealing temperature into a tank of water at ambient temperature.

After that, shaping and machining operations are carried out, in cold conditions, that is to say at ambient temperature. This step is aimed at forming the ingot into the shape of the required device or element, for a biomedical application as mentioned above. The forming operation is of course adapted to the configuration and shape of the product to make and uses known machining techniques or forming techniques such as drawing, rolling, extrusion or other techniques.

The biomedical device thus manufactured and made of the required alloy is then subjected to thermal treatment for redissolution above the temperature TB which is the beta transus temperature, typically between 600° C. and 1050° C.

The device is maintained at that temperature for a period of a few tens of minutes to a few hours, in a gaseous atmosphere such as nitrogen for example. The device used is a stove known in itself The treatment is at constant temperature and has two objectives:
  making a beta recrystallized microstructure with a finer grain size in order to improve and optimize the mechanical properties of the final biomedical device;
  depositing, during the treatment in the oven, of a nitride coat on the surface of the device, through a direct hot reaction between the alloy of which the device is made and the gaseous nitrogen introduced in the quenching oven. This treatment is a nitriding process in gaseous phase.

The duration of this nitriding step varies from 0.5 to 10 hours depending on the compositions of the alloys, the required thicknesses and the shape of the device. The temperature maintained during this nitriding step ranges between 600 and 1050° C.

Lastly, at the end of the nitriding/recrystallizing phase, a second quench is carried out, preferably with water, to bring the temperature of the device down to the ambient temperature. That second quench makes it possible to maintain the beta microstructure of the alloy in a metastable form.

The applicant has carried out laboratory tests on samples of alloy made using the method according to the invention described above. The alloy in question is superelastic of the recrystallized beta-metastable type with a grain size between 10 and 60 microns (see the beta microstructure at the core of the alloy in FIG. 2). Its composition stated by mass percentage is: Ti (50%), Ta (25%) and Nb (25%). The recrystallization-nitriding phase carried out at 800° C. for three hours leads to the application of a coat of titanium nitride that is a few microns thick. The microstructure of the nitride on the surface is shown in a cross-section in FIG. 3, where the dark parts correspond to the nitrided area made up of nitrogen-rich needles (internal nitriding).

Figure 4:
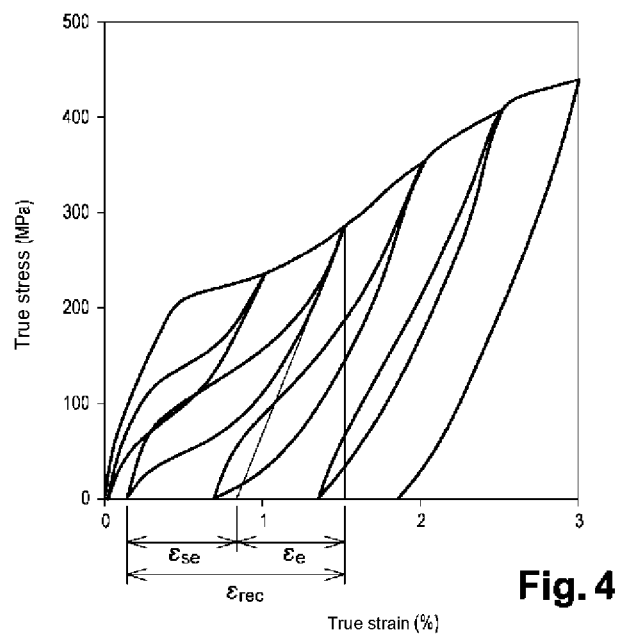
FIG. 4 shows a cycled (successive loading/unloading) single-axis tension curve showing the superelastic nature of the nitrided alloy by the formation of hysteresis between loading and unloading due to stress-induced alpha" martensitic transformation.

The fine coat of nitride does not affect the superelastic properties of the alloy made in this way. FIG. 4 shows the cycled tension curve for nitrided alloy, which shows the presence of loading/unloading hysteresis characteristic of the superelastic effect. The cycled tension test shown in this figure was carried out on a one-millimeter thick flat specimen obtained using this manufacturing method. The load/unload cycles were carried out with a 0.5% deformation increment.

Compared to a non-nitrided alloy with the same composition, a nitrided alloy made using the method according to the invention shows an increased surface hardness (Vickers micro hardness measured to be 4 times greater), which leads to a very strong increase in wear resistance (85% less wear volume) and a clear decrease in the friction coefficient (divided by 5). FIGS. 5A and 5B each show a top view of a sample alloy that has undergone a scratch test, non-nitrided (5A—prior art) and nitrided (5B—according to the invention) respectively. The furrows (dark in color) are obtained with a 25 g load after 200 rotation cycles using a pin on disc tribometer. It can be seen that the alloy according to the invention (FIG. 5B) has much greater surface resistance.

The nitriding phase carried out in the gaseous phase as described above has several benefits compared to known nitriding techniques.
  The depositing of a substantially even coat of nitride, including on objects with complex shapes, as are most devices for biomedical use;
  Great simplicity of application;
  Nitriding (that is to say depositing nitride) is carried out simultaneously with the recrystallization of the alloy during dissolution; this is not possible using the other nitriding methods, which can only be carried out after vacuum recrystallization.
  Very high bonding of the coat on the alloy by the formation of internal nitriding close to the surface.

Further, the second quench of the method according to the invention, which follows the simultaneous step of nitriding/recrystallization, offers the advantage of maintaining the beta metastable microstructure at the core of the alloy, to obtain the superelastic effect.

The invention is not limited to the depositing of nitride, but also includes the depositing of a surface coat of oxide, oxynitride or carbonitride. In that case, an appropriate gas or gas mixture is used, in this case oxygen for an oxide coat, or by adding carbon dioxide, nitrogen monoxide or even air for obtaining oxynitride or carbonitride on the surface.

The alloy made using the method according to the invention in accordance with the stated compositions has the following benefits compared to titanium/nickel type alloys, particularly very large cold deformation capability and greater machinability, which two benefits are particularly appreciated in the case of devices for biomedical applications. As an example, endodontic files according to the prior art show relatively high wear and significant risks of breaking caused by machining grooves.

Further, the cutting capability of the alloy according to the invention is greater than that of alloys of the prior art. The nitride coat improves the properties of hardness and wear resistance, while providing beneficial effects in terms of biocompatibility. In devices for cardiovascular applications such as stents, better biocompatibility is observed in the alloy according to the invention. Lastly, the biomedical device made in this manner offers greater resistance to sterilization operations and is less sensitive to bacteriological activity thanks to the presence of the nitride coat.

To sum up, the method according to the invention makes it possible to manufacture a titanium alloy for biomedical applications that has superelastic and/or shape memory properties, with all the attendant benefits stated above, and further, some of these properties are themselves reinforced by the nitride coat, which itself brings other mechanical properties or capabilities, and lastly that coat reinforces or improves the biocompatibility of the device for biomedical use.

What is claimed is:

1. A method for manufacturing a titanium alloy with no nickel and with superelastic and/or shape memory properties for biomedical applications, comprising the steps of:
   preparing an ingot of the titanium alloy by vacuum melting the the titanium alloy;
   performing a vacuum homogenization of the ingot by annealing the ingot at a first temperature, wherein the annealing comprises raising the temperature of the ingot and holding it at that temperature for a period that allows full homogenization;
   performing a first quenching of the vacuum homogenized ingot;
   performing a mechanical shaping of the ingot at an ambient temperature into a predetermined shape;
   performing a heat treatment of the ingot for redissolution in a beta phase beyond the beta transus temperature, the heat treatment comprising raising the temperature up to a second required temperature and holding at that temperature for a certain period; and
   performing a second quenching of the ingot;
   wherein the method is characterized in that said heat treatment is carried out in a gaseous atmosphere and the heat treatment further comprises a nitriding phase wherein a surface treatment is applied to the ingot through a reaction with one or more gases in the gaseous atmosphere, so as to form a coat of nitride, carbonitride or oxynitride evenly on one or more surfaces of the ingot.

2. The method according to claim 1, wherein the nitriding phase is carried out at a temperature ranging between 600° C. and 1050° C.

3. The method according to claim 2, wherein the nitriding phase is carried out at a temperature ranging between 800° C. and 1050° C.

4. The method according to claim 1 wherein the duration of holding at the annealing temperature of the homogenization step ranges between 12 and 20 hours.

5. The method according to claim 4, wherein the duration of holding at the annealing temperature of the homogenization step is about 16 hours.

6. The method according to claim 1 wherein the nitriding phase is carried out in a nitrogen atmosphere.

7. The method according to claim 1 wherein the nitriding phase is combined with a simultaneous phase of recrystallization.

8. The method according to claim 1 wherein the homogenization step is carried out at a temperature above 900° C.

9. The method according to claim 1 wherein the first and second quenches are carried out either with water or with air.

* * * * *